(12) United States Patent
Takahashi et al.

(10) Patent No.: US 12,016,259 B2
(45) Date of Patent: Jun. 25, 2024

(54) INFORMATION PROVIDING DEVICE, MOWING VEHICLE AND MOWING MANAGEMENT SYSTEM

(71) Applicant: HONDA MOTOR CO., LTD., Tokyo (JP)

(72) Inventors: Hiroto Takahashi, Wako (JP); Toshiaki Kawakami, Wako (JP); Taro Yokoyama, Wako (JP); Wei Song, Wako (JP); Takuya Kanisawa, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 627 days.

(21) Appl. No.: 17/210,563

(22) Filed: Mar. 24, 2021

(65) Prior Publication Data
US 2021/0298229 A1 Sep. 30, 2021

(30) Foreign Application Priority Data
Mar. 27, 2020 (JP) .................. 2020-057076

(51) Int. Cl.
*A01C 21/00* (2006.01)
*A01B 79/02* (2006.01)
(Continued)

(52) U.S. Cl.
CPC ............ *A01C 21/007* (2013.01); *A01B 79/02* (2013.01); *A01D 34/008* (2013.01); *A01D 34/64* (2013.01);
(Continued)

(58) Field of Classification Search
CPC ..... A01B 79/005; A01B 79/02; A01C 21/007; A01D 34/64; A01D 34/78; A01D 2101/00;
(Continued)

(56) References Cited

U.S. PATENT DOCUMENTS 5,841,883 A * 11/1998 Kono ....................... A01G 7/00
   382/110
8,634,960 B2 * 1/2014 Sandin .................. B60L 3/0023
   700/258
(Continued)

FOREIGN PATENT DOCUMENTS

BR   112017026437 B1 * 1/2022 ........... A01B 79/005
CA   2748079 A1 * 2/2012 ............... G06N 5/04
(Continued)

OTHER PUBLICATIONS

Japanese Office Action for Japanese Patent Application No. 2020-057076 dated Aug. 8, 2023.

*Primary Examiner* — Arpad Fabian-Kovacs
(74) *Attorney, Agent, or Firm* — Amin, Turocy & Watson, LLP

(57) ABSTRACT

An information providing device includes an information acquisition part configured to acquire environment information which indicates a growth environment of grass in a predetermined area and state information which indicates a growth state of the grass in the predetermined area, and an information generating part configured to determine a good area which indicates an area in which the growth state of the grass in the predetermined area is good and a bad area which indicates an area in which the growth state of the grass in the predetermined area is bad based on the state information, and configured to generate management information which indicates a content of treatments to be performed with respect to the good area and the bad area based on the environment information.

10 Claims, 11 Drawing Sheets

(51) Int. Cl.
    *A01D 34/00*     (2006.01)
    *A01D 34/64*     (2006.01)
    *A01G 7/06*     (2006.01)
    *G01N 33/00*     (2006.01)
    *G05D 1/00*     (2006.01)
    *G06F 17/18*     (2006.01)
    *A01B 79/00*     (2006.01)
    *A01D 34/78*     (2006.01)
    *A01D 101/00*     (2006.01)
    *G05B 13/04*     (2006.01)

(52) U.S. Cl.
    CPC ............ *A01G 7/06* (2013.01); *G01N 33/0098* (2013.01); *G05D 1/0219* (2013.01); *G06F 17/18* (2013.01); *A01B 79/005* (2013.01); *A01D 34/78* (2013.01); *A01D 2101/00* (2013.01); *G05B 13/048* (2013.01)

(58) Field of Classification Search
    CPC ............. A01D 34/008; G01N 33/0098; G05B 13/048; G05D 1/0219; G05D 2201/0208; G06F 17/18
See application file for complete search history.

(56) References Cited

U.S. PATENT DOCUMENTS

| | | | |
|---|---|---|---|
| 11,763,457 B2 * | 9/2023 | Ogawa | A01G 7/00 382/110 |
| 2013/0136312 A1 | 5/2013 | Tseng et al. | |
| 2016/0063420 A1 | 3/2016 | Tomii et al. | |
| 2017/0287082 A1 | 10/2017 | Karube et al. | |
| 2017/0303466 A1 * | 10/2017 | Grufman | G06T 7/80 |
| 2019/0141887 A1 | 5/2019 | Matsuda et al. | |
| 2019/0333214 A1 | 10/2019 | Haneda et al. | |
| 2020/0201269 A1 * | 6/2020 | Johannesson | A01B 79/02 |
| 2020/0347581 A1 | 11/2020 | Shimamura et al. | |

FOREIGN PATENT DOCUMENTS

| | | | | |
|---|---|---|---|---|
| DE | 102013203705 A1 * | 9/2014 | | A01D 34/008 |
| JP | 07-115846 | 5/1995 | | |
| JP | 2011142844 A * | 7/2011 | | A01D 34/006 |
| JP | 2013-111078 | 6/2013 | | |
| JP | 5783678 | 9/2015 | | |
| JP | 2016-010398 | 1/2016 | | |
| JP | 2016-049102 | 4/2016 | | |
| JP | 2018-108041 | 7/2018 | | |
| JP | 2019-088252 | 6/2019 | | |
| WO | 2016/178268 | 11/2016 | | |
| WO | WO-2017004074 A1 * | 1/2017 | | A01G 2/00 |
| WO | 2019/167207 | 9/2019 | | |
| WO | WO-2019167204 A1 * | 9/2019 | | G05D 1/0044 |
| WO | WO-2019167209 A1 * | 9/2019 | | G05D 1/02 |

* cited by examiner

| A | B |
|---|---|
| PHOTOGRAPHED IMAGE OF MOWING REGION | MANAGEMENT INFORMATION |
| 0001.jpg~1000.jpg | TRAVELING LIMIT |
| 1001.jpg~2000.jpg | SPRAYING OF MEDICINE FOR LARGE PATCH |
| 2001.jpg~3000.jpg | SPRAYING OF MEDICINE FOR RUST DISEASE |
| 3001.jpg~4000.jpg | TREATMENT NOT NECESSARY |

INFORMATION PROVIDING DEVICE, MOWING VEHICLE AND MOWING MANAGEMENT SYSTEM

CROSS-REFERENCE TO RELATED APPLICATION

Priority is claimed on Japanese Patent Application No. 2020-057076, filed Mar. 27, 2020, the content of which is incorporated herein by reference.

BACKGROUND OF THE INVENTION

Field of the Invention

The present invention relates to an information providing device, a mowing vehicle and a mowing management system.

Description of Related Art

Lawn mowers include a hand-push type lawn mowing vehicle operated by a worker located behind the vehicle, a riding lawn mowing vehicle driven by a boarded worker, and the like. A technology of detecting a growing state of a lawn using such a lawn mower is being studied. For example, as a technique of automatically detecting a growing state of a lawn, a technology of detecting a state of a lawn before mowing using a sensor and creating data showing a growing situation of the lawn on the basis of the detection result is disclosed (for example, see Japanese Patent No. 5783678).

SUMMARY OF THE INVENTION

However, when there are areas where growth of a lawn is not good, a technology of appropriately dealing with such areas has not been sufficiently examined.

An aspect of the present invention is directed to providing a technology capable of appropriately dealing with an area in which growth of a lawn is not good.

According to an aspect of the present invention, there is provided an information providing device including an information acquisition part configured to acquire environment information which indicates a growth environment of a lawn in a predetermined area and state information which indicates a growth state of the lawn in the predetermined area, and an information generating part configured to determine a good area which indicates an area in which the growth state of the lawn in the predetermined area is good and a bad area which indicates an area in which the growth state of the lawn in the predetermined area is bad based on the state information, and configured to generate management information which indicates a content of treatments to be performed with respect to the good area and the bad area based on the environment information.

According to the aspect of the present invention, it is possible to more appropriately deal with an area in which growth of a lawn is not good.

DETAILED DESCRIPTION OF THE INVENTION

Figure 1:
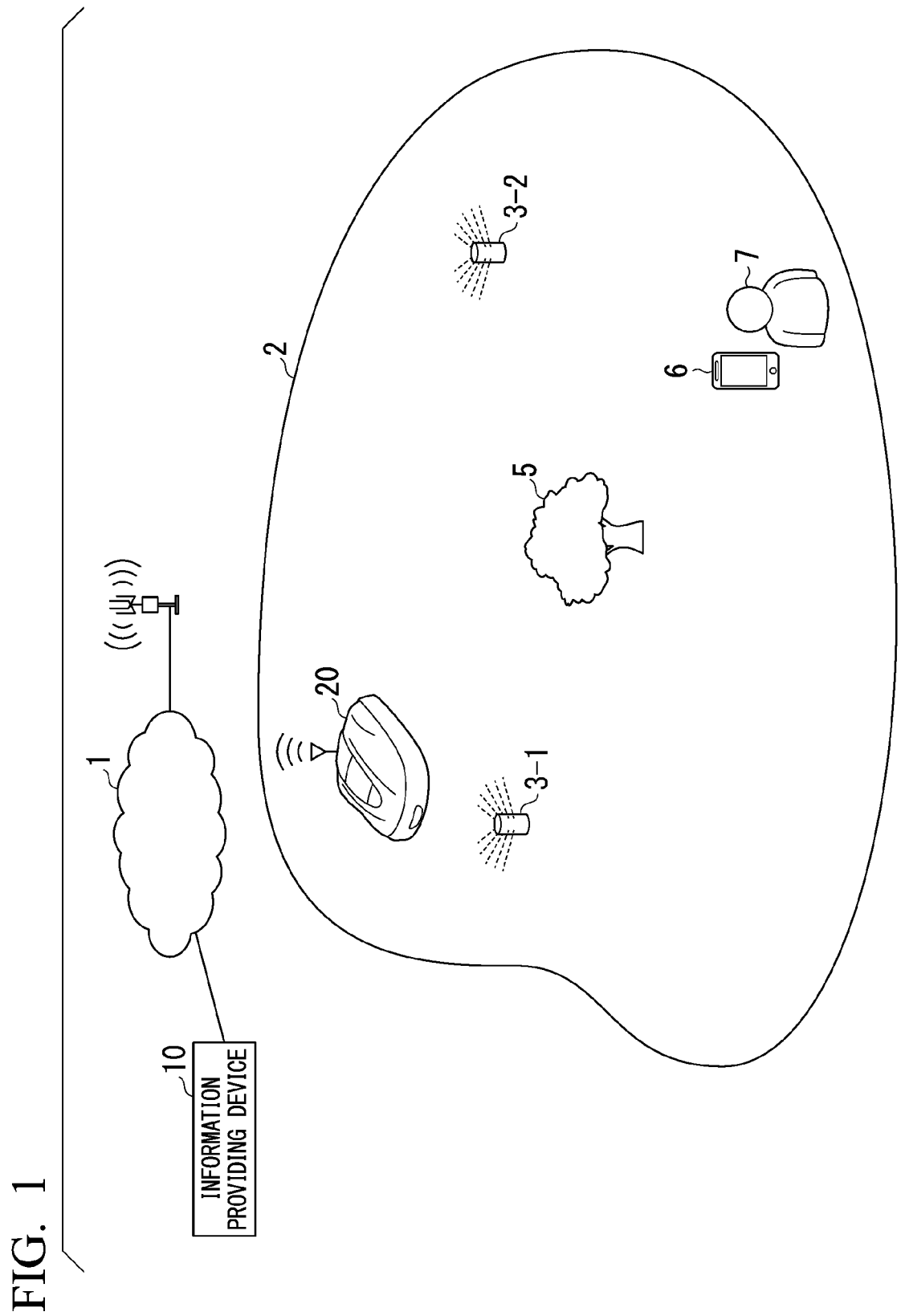
FIG. 1 is a configuration view of a lawn mowing management system according to a first embodiment of the present invention.

Hereinafter, embodiments will be described in detail with reference to the accompanying drawings. Further, the following embodiments do not limit the invention related to the scope of the claims, and not all combinations of features described in the embodiments are essential for the invention. Two or more features of a plurality of features described in the embodiments may be arbitrarily combined. In addition, the same or similar components are designated by the same reference numerals, and overlapping description will be omitted. Further, in the embodiments, a lawn is a lawn of grass. Lawn grass is an example of grass, and other examples of grass are weeds or the like.

First Embodiment

FIG. 1 is a configuration view of a lawn mowing management system according to a first embodiment of the present invention. As shown in FIG. 1, a lawn mowing management system according to the first embodiment of the present invention includes an information providing device 10, a plurality of sprinklers 3 (for example, a sprinkler 3-1 and a sprinkler 3-2), a terminal device 6 and a lawn mowing vehicle 20. Devices included in the management system are connected so that data can be communicated. For example, the information providing device 10, the terminal device 6 and the lawn mowing vehicle 20 are communicatively connected to each other via a communication network 1. The communication network 1 may be a wired communication system such as an optical fiber or an electric communication line pursuant to a standard specification such as Ethernet (registered trademark) or the like, or a wireless communication system such as Long Term Evolution (LTE) (registered trademark), a fifth generation wireless communication system, or a wireless LAN system.

The management system performs management related to growing of lawn in a management target area 2.

The management target area 2 shows an area that is a target of management related to growing of lawn. The management target area 2 is evaluated as any one of a plurality of state candidates according to a growth state of a lawn. In the embodiment, the management target area 2 is defined in advance by dividing it into a plurality of subsidiary areas, and the state is evaluated for each subsidiary area. For example, four types of state candidates may be defined as a first state, a second state, a third state and a fourth state.

The first state is a state in which a growing state is worst. The first state is, for example, a state in which the lawn has not grown enough and the soil is visible. A second state is a state in which the growing state is the second worst after the first state. The second state is, for example, a state in which the lawn is growing but a disease is occurring, or a state in which the lawn is dying. A third state is a preferred state in which the lawn is properly growing. The third state is, for example, a state in which the lawn is growing and a color or a length also satisfies a predetermined condition. A fourth state is a state in which the lawn has excessively grown, which is not very preferable. The fourth state is, for example, a state in which the lawn is growing, but its length exceeds a predetermined condition.

In the following description, an area evaluated as the first state is referred to as a first area, an area evaluated as a second state is referred to as a second area, an area evaluated as the third state is referred to as a third area, and an area evaluated as the fourth state is referred to as a fourth area. The subsidiary areas of the management target area 2 are appropriately managed by a manager 7 according to the evaluated content.

The manager 7 manages the lawn by performing lawn mowing, growing of the lawn, or the like, in the management target area 2. The manager 7 may acquire management information that manages a growth state of the lawn in the management target area 2 from the terminal device 6.

The management information is, for example, information indicating a predetermined amount of water sprinkling or fertilization in a predetermined area in the management target area 2. The management information may be, for example, information indicating limitation of traveling of the lawn mowing vehicle 20, or information instructing an increase in an amount of solar radiation through pruning of trees. The management information may be information instructing to mow the lawn or weeds that have grown excessively. The manager 7 executes treatment for improving a growth state of the lawn in the management target area 2 on the basis of the management information.

The information providing device 10 acquires environment information indicating a growth environment of the lawn, and state information showing a growth state of the lawn. The environment information is information related to an environment that has a probability of exerting an influence on growing of the lawn. The environment information may be, for example, information indicating an amount of solar radiation, information indicating an air volume, information indicating an amount of rainfall, humidity or an amount of moisture in the soil, information indicating a nutrient amount in the soil, a particle size of soil particles, or acidity of the soil.

The state information is information indicating the current state of the lawn. The state information may be, for example, information indicating a height of the lawn, or may also be information indicating that the lawn suffers from a certain disease. The environment information and the state information may also be acquired by the lawn mowing vehicle 20. For example, the information indicating a height of the lawn may be obtained on the basis of, for example, a load applied to a cutting part 25 of the lawn mowing vehicle 20 and a height of the cutting part 25 upon lawn mowing.

The sprinkler 3-1 and the sprinkler 3-2 perform a predetermined amount of water sprinkling in the management target area 2 through an operation of the manager 7.

The terminal device 6 is an information device such as a smart phone, a tablet computer, a personal computer, or the like. The terminal device 6 may be configured using a portable device or a stationary device.

Figure 2:
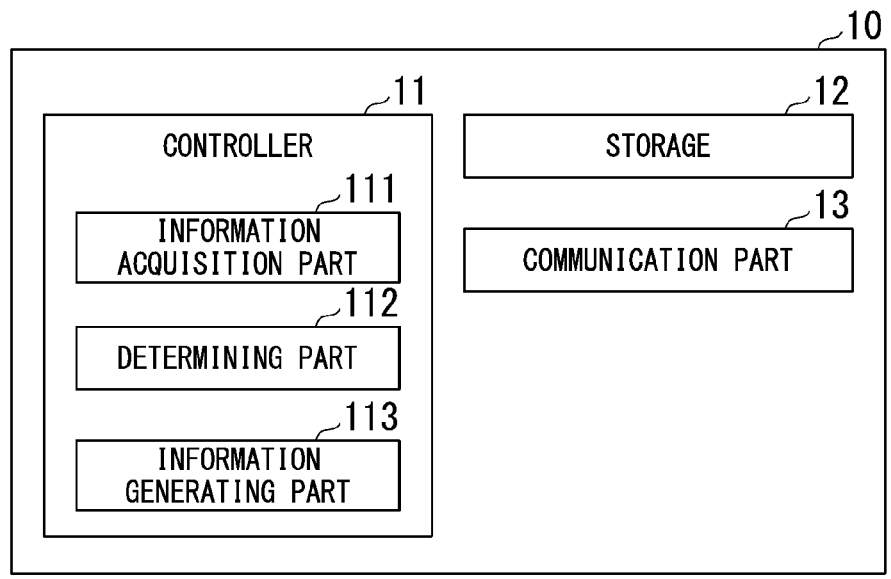
FIG. 2 is a functional block diagram of an information providing device according to the first embodiment of the present invention.

FIG. 2 is a functional block diagram of the information providing device 10 according to the first embodiment of the present invention. The information providing device 10 includes a controller 11, a storage 12 and a communication part 13. The controller 11 is configured using a processor such as a central processing unit (CPU) or the like, or a memory. The controller 11 functions as an information acquisition part 111, an information generating part 113 and a determining part 112 when the processor executes a program.

The storage 12 is, for example, a memory module including a RAM, a ROM, hard disk drive (HDD), a solid state drive (SSD), an electrically erasable programmable ROM (EEPROM), or the like. Further, the storage 12 is not limited to a built-in type, and may be an external memory module connected by a digital input/output port or the like such as a Universal Serial Bus (USB) or the like.

The communication part 13 may be a wired communication interface using an optical fiber, a coaxial cable or a twisted-pair wire as a medium pursuant to a standard specification such as Ethernet (registered trademark) or the like, or may be a wireless communication interface such as Long Term Evolution (LTE) (registered trademark), a fifth generation wireless communication system or a wireless LAN system.

The information acquisition part 111 acquires environment information and state information of the lawn in the management target area 2, and stores them in the storage 12. The information acquisition part 111 may acquire environment information and state information from the outside via the communication network 1 using the communication part 13, or may acquire the environment information and state information via a keyboard, a mouse, or a touch screen panel of a display device connected to the information providing device 10.

The determining part 112 determines whether a growth state of the lawn is good or a growth state of the lawn is bad on the basis of the acquired state information, and stores the result in the storage 12. The determining part 112 may compare a value indicated by the acquired state information with a predetermined reference value or threshold or may compare pieces of state information acquired in the plurality of subsidiary areas with each other when the growth state of the lawn is determined.

The information generating part 113 generates good area information indicating an area with a good growth state of the lawn, and bad area information indicating an area with a bad growth state of the lawn for each areas, on the basis of the determined result stored in the storage 12, and stores them in the storage 12.

Figure 3:
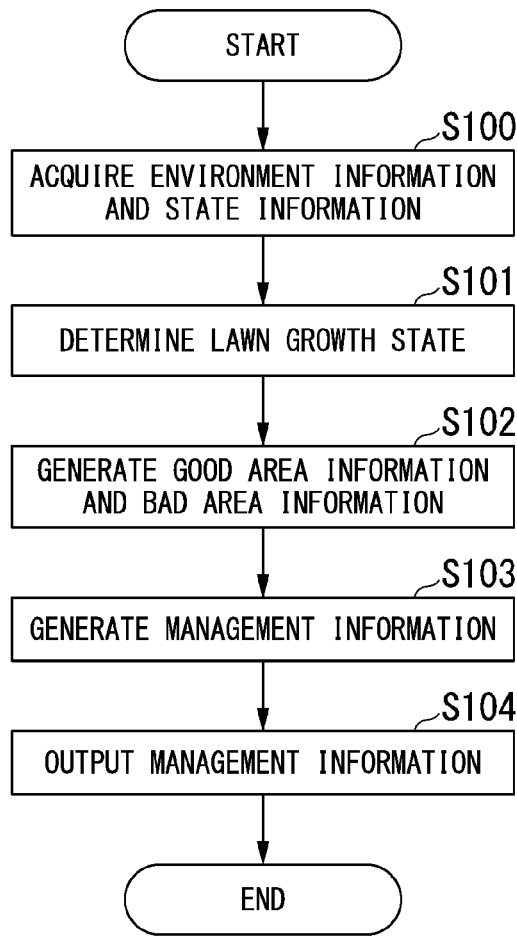
FIG. 3 is a flowchart showing a basic operation of the information providing device according to the first embodiment of the present invention.

FIG. 3 is a flowchart showing a basic operation of the information providing device 10 according to the first embodiment of the present invention. In step S100, the information acquisition part 111 acquires environment information of the lawn in the management target area 2, and stores it in the storage 12. In addition, in step S100, the information acquisition part 111 acquires state information, and stores it in the storage 12. In step S101, the determining part 112 determines whether the growth state of the lawn is good or the growth state of the lawn is bad in each area on the basis of the acquired state information, and stores the result in the storage 12.

In S102, the information generating part 113 generates good area information indicating an area with a good growth state of the lawn and bad area information indicating an area with a bad growth state of the lawn for each areas on the basis of the determined result stored in the storage 12, and stores them in the storage 12. The information generating part 113 advances processing to step S102. In step S103, the information generating part 113 generates management information indicating treatments corresponding to the environment information, the good area information and the bad area information, and stores it in the storage 12. In step S104, the information acquisition part 111 outputs the management information. In outputting of the management information, the information generating part 113 may output or transmit the management information to the outside using the communication part 13. The information generating part 113 terminates the processing after that.

Figure 4:
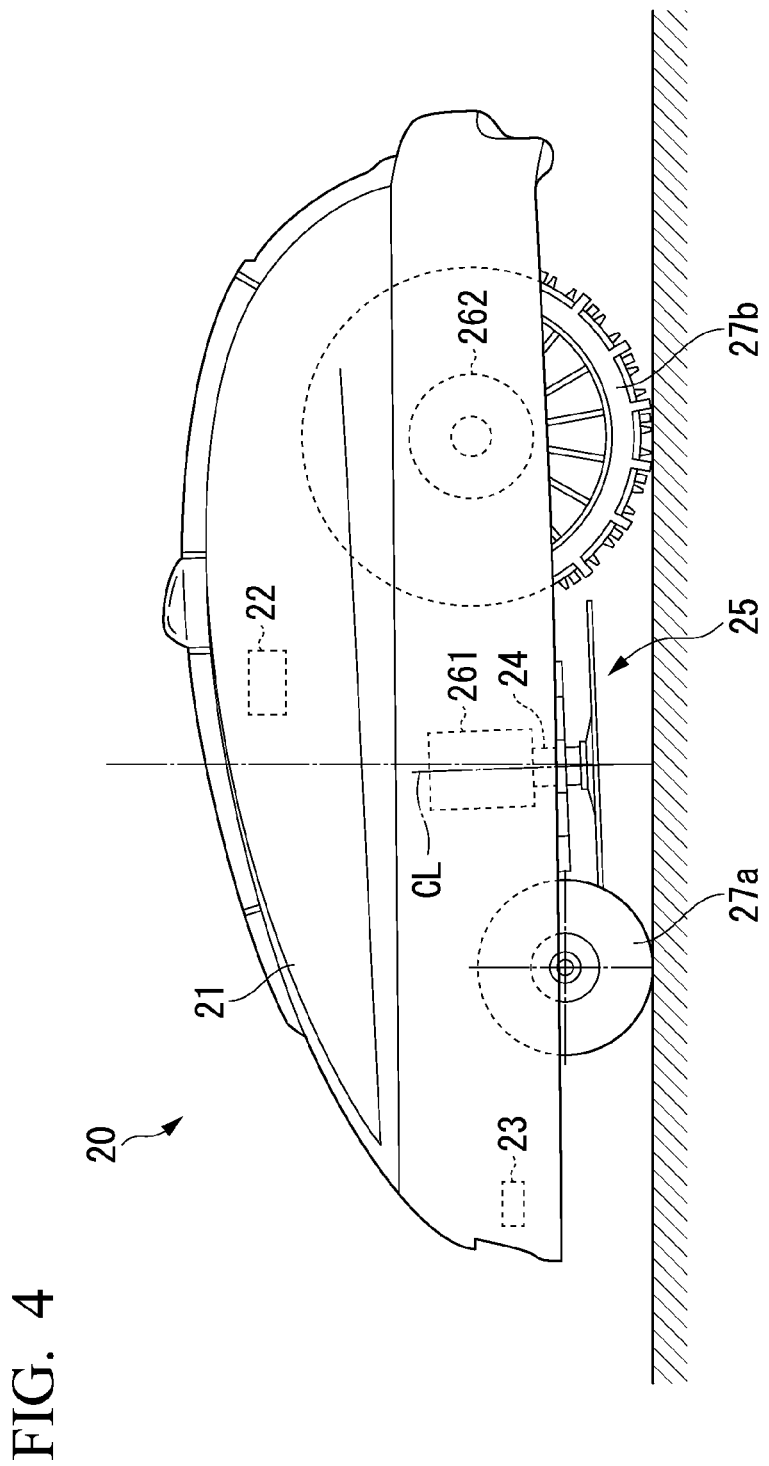
FIG. 4 is a configuration view of a lawn mowing vehicle according to the first embodiment of the present invention.

FIG. 4 is a configuration view of the lawn mowing vehicle 20 according to the first embodiment of the present invention. The lawn mowing vehicle 20 includes a display 21, a controller 22, a sensor 23, a rotating shaft 24, the cutting part 25, a motor 26, and wheels including a front wheel 27a and a rear wheel 27b. The motor 26 includes a cutting part driving motor 261 and a wheel motor 262. The lawn mowing vehicle 20 mows a lawn or grass using the cutting part 25 while traveling by the front wheel 27a and the rear wheel 27b. The lawn mowing vehicle 20 may be an autonomous traveling type that operates by itself without a manual operation, or a manual type that is manually operated by a person. The lawn mowing vehicle 20 may be a riding type operated by a person on board.

Figure 5:
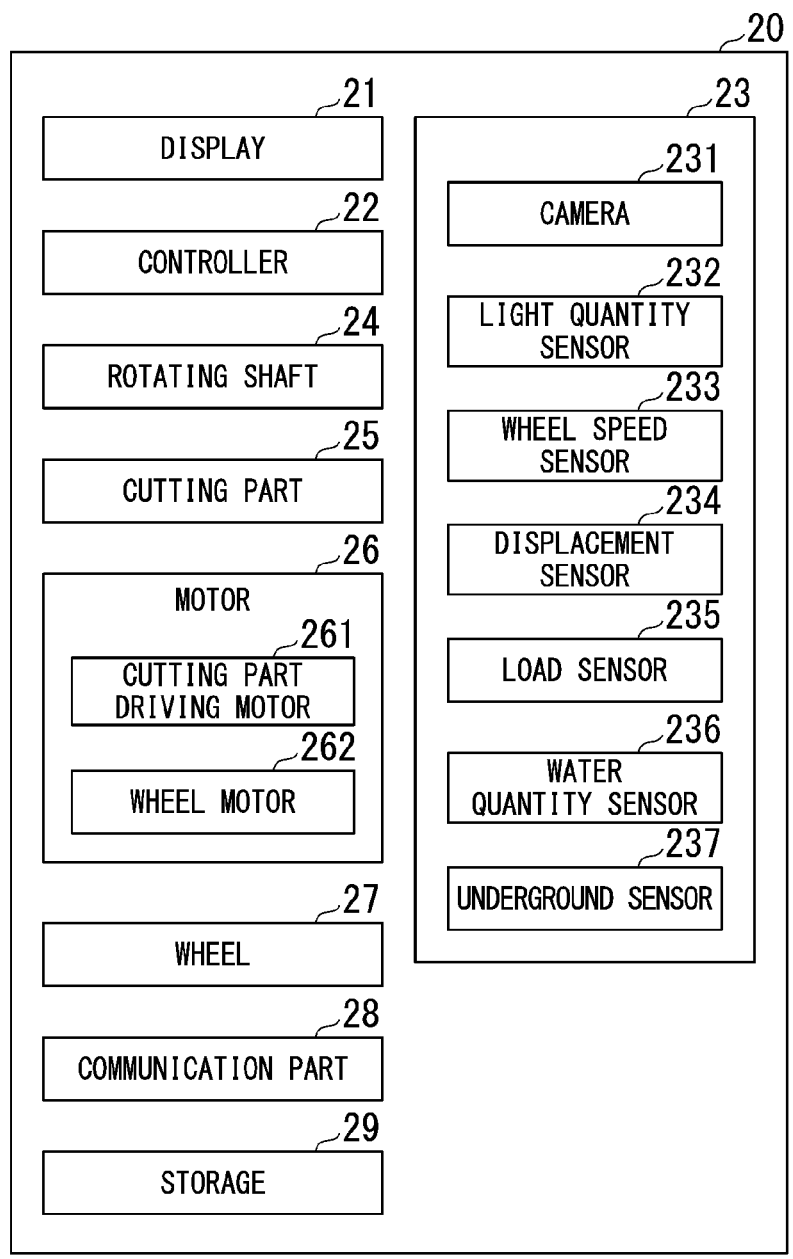
FIG. 5 is a functional block diagram of the lawn mowing vehicle according to the first embodiment of the present invention.

FIG. 5 is a functional block diagram of the lawn mowing vehicle 20 according to the first embodiment of the present invention. In addition to FIG. 4, the lawn mowing vehicle 20 includes a communication part 28 and a storage 29. The lawn mowing vehicle 20 may include a camera 231, a light quantity sensor 232, a wheel speed sensor 233, a displacement sensor 234, a load sensor 235, a water quantity sensor 236 and an underground sensor 237, as the sensor 23. The display 21 is a display element such as a liquid crystal or an organic EL. The display 21 displays information related to a state, maintenance or management of the lawn mowing vehicle 20.

The controller 22 controls operations of the lawn mowing display 21, the sensor 23, the cutting part 25, the motor 26, the wheels 27 or the communication part 28. The camera 231 photographs an image of the management target area 2, and stores it in the storage 29 as the state information or the environment information. The light quantity sensor 232 is a photoelectric transducer, acquires an amount of solar radiation in the management target area 2, and stores it in the storage 29 as the environment information.

The wheel speed sensor 233 acquires a traveling speed and a temporal change thereof of the lawn mowing vehicle 20, and stores them in the storage 29. The displacement sensor 234 may be any one of a contact type, a built-in camera laser type, a reflective laser type and a transmissive laser type. The displacement sensor 234 detects a height of an object. The object may be a lawn or may be the cutting part 25. The displacement sensor 234 detects a height of the cutting part 25 and stores it in the storage 29 as the state information. The load sensor 235 detects any one of a current and a heat quantity. The load sensor 235 detects a load applied to the cutting part 25, and stores it in the storage 29 as the state information. Here, the load applied to the cutting part 25 can be used as the state information because the load is increased when the lawn is actively growing.

The motor 26 is an electric motor, which is a driving source configured to drive the cutting part 25 and the wheels 27. However, in the embodiment, the motor 26 is not limited to the electric motor and may be a prime mover driven by an engine. The cutting part 25 includes a blade formed of a metal or a fiber, and mows a lawn or grass by rotating the blade. The cutting part 25 is elevatably supported, and can mow the lawn or the grass at a desired height. The communication part 28 reads the state information or the environment information stored in the storage 29 and transmits it to the outside. The configuration of the storage 29 is the same as that of the storage 12. The configuration of the communication part 28 is the same as that of the communication part 13.

Figure 6:
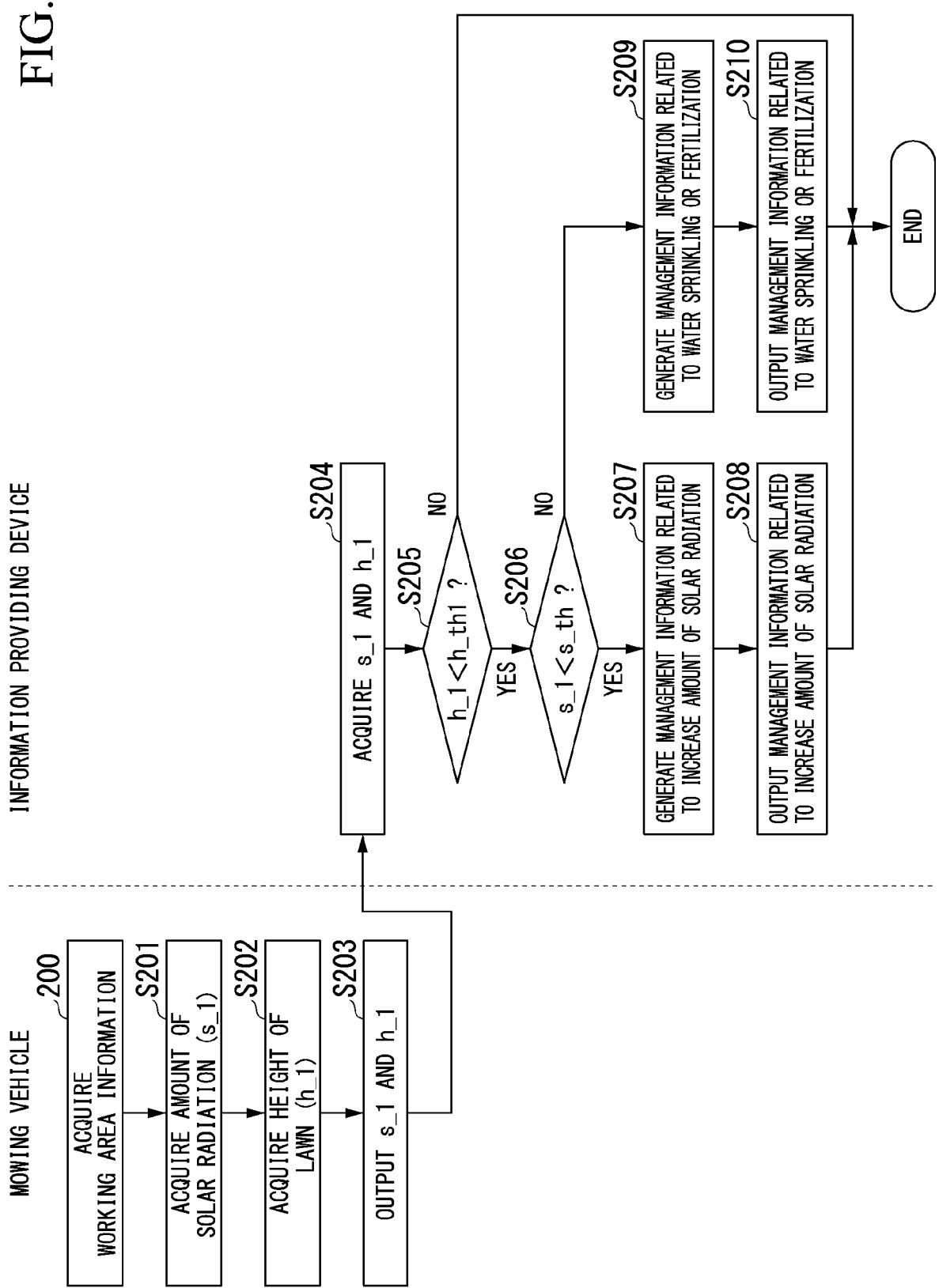
FIG. 6 is a flowchart showing an operation of the information providing device and the lawn mowing vehicle according to the first embodiment of the present invention.

FIG. 6 is a flowchart showing operations of the information providing device 10 and the lawn mowing vehicle 20 according to the first embodiment of the present invention. First, sequence of acquisition and transmission of environment information and state information by the information providing device 10 will be described. In step S200, the controller 22 acquires information of subsidiary areas, and stores it in the storage 29. In step S201, the light quantity sensor 232 acquires an amount of solar radiation $s\_1$ in the subsidiary area, and stores it in the storage 29 as the environment information. The light quantity sensor 232 may acquire the amount of solar radiation $s\_1$ at one place of the subsidiary area, or may acquire the place of the plurality of places in the subsidiary area.

In step S202, the displacement sensor 234 detects a height $h\_1$ of the cutting part 25 in the subsidiary area, and stores it in the storage 29 as the state information. Here, the height of the cutting part 25 is a height at which the load sensor 235 detects a predetermined load upon lawn mowing. Accordingly, the height of the cutting part 25 indicates the height $h\_1$ of the lawn in the subsidiary area.

In step S203, the communication part 28 reads the $s\_1$ and $h\_1$ from the storage 29, and transmits them to the information providing device 10 via the communication network 1.

Next, operations of the information providing device 10 which acquires environment information and state information and which generates and outputs management information on the basis of the environment information and the state information will be described. In step S204, the communication part 13 acquires the $s\_1$ and $h\_1$ via the communication network 1, and stores them in the storage 12. In step S205, the information acquisition part 111 reads the $s\_1$ and $h\_1$ from the storage 12.

In step S205, the determining part 112 determines whether $h\_1$ is less than $h\_th1$. The $h\_th1$ is a first threshold related to the height of the lawn, which relates to the growth of the lawn. The determining part 112 determines that the subsidiary area is a first area or a second area, which is an area of bad growth, when the height $h\_1$ of the lawn is less than $h\_th1$. The information generating part 113 generates bad area information, and stores it in the storage 12. The information generating part 113 advances the processing to step S206. Meanwhile, the determining part 112 determines that the subsidiary area is a third area or a fourth area, which is at least an area of good growth, when the height $h\_1$ of the lawn is equal to or greater than $h\_th1$, and the information generating part 113 generates good area information and stores it in the storage 12. After that, the information generating part 113 terminates the processing.

The fact that processing has advanced to step S206 means that the growth of the lawn in the subsidiary area is bad and the subsidiary area is the first area or the second area. In step S206, the determining part 112 performs evaluation of the amount of solar radiation $s\_1$ in the subsidiary area. The determining part 112 determines whether $s\_1$ is less than $s\_th$. The $s\_th$ is a threshold used to determine whether the amount of solar radiation is sufficient. The determining part 112 advances the processing to step S207 when $s\_1$ is less than $s\_th$. Meanwhile, the determining part 112 advances the processing to step S209 when $s\_1$ is equal to or greater than $s\_th$. In step S207, the information generating part 113 generates management information instructing an increase in amount of solar radiation in the subsidiary area, and advances the processing to step S208. In step S208, the information generating part 113 outputs management information instructing an increase in amount of solar radiation in the subsidiary area, and terminates the processing.

The fact that the processing advances to step S209 means that the growth of the lawn in the subsidiary area is bad but the amount of solar radiation is sufficient. In step S209, the information generating part 113 generates management information instructing a predetermined amount of water sprinkling or a predetermined amount of fertilization in the subsidiary area, and stores it in the storage 12. In step S210, the information generating part 113 outputs the management information instructing the predetermined amount of water sprinkling or the predetermined amount of fertilization in the subsidiary area.

The communication part 13 transmits the management information generated and output by the information generating part 113 to the terminal device 6 via the communication network 1. The manager 7 performs treatment corresponding to the management information on the basis of the management information displayed on the terminal device 6. For example, the manager 7 may prune a tree 5 disposed in the vicinity of the subsidiary area on the basis of the management information instructing an increase in amount of solar radiation of the subsidiary area. Pruning of the tree 5 contributes to the increase in amount of solar radiation in the subsidiary area.

The manager 7 may increase an amount of water sprinkling in the subsidiary area using the sprinkler 3-1 or the sprinkler 3-2 on the basis of the management information instructing the water sprinkling or fertilization in the subsidiary area. Alternatively, the manager 7 may increase the amount of fertilizer sprinkled in the subsidiary area.

As described above, the information providing device 10 according to the embodiment includes the controller 11, the storage 12 and the communication part 13. The controller 11 includes the information acquisition part 111, the information generating part 113 and the determining part 112. The information acquisition part 111 acquires environment information and state information in the subsidiary area of the management target area 2. The information generating part 113 generates good area information and bad area information in the subsidiary area on the basis of the state information, and generates management information indicating treatments corresponding to the environment information, the good area information and the bad area information.

According to the configuration, it is possible to identify causes of growth deterioration in an area in which the growth of the lawn is not good, and provide the management information regarding the treatment with respect to the identified causes of growth deterioration.

In addition, the lawn mowing vehicle 20 may detect an amount of moisture $w\_1$ in the subsidiary area using the water quantity sensor 236, and store it in the storage 29 as the environment information. The communication part 28 transmits the environment information to the information providing device 10 via the communication network 1. The information generating part 113 generates good area information and bad area information on the basis of the state information and the environment information. The information generating part 113 generates management information corresponding to the environment information, the good area information and the bad area information.

In this case, the water quantity sensor 236 and the information acquisition part 111 acquire environment information and state information by replacing each $s\_1$ in FIG. 6 with $w\_1$. The determining part 112 generates good area information and bad area information by replacing $s\_1$ and $s\_th$ in FIG. 6 with $w\_1$ and $w\_th$, respectively. The $w\_th$ is a threshold amount of moisture used to determine whether the amount of moisture in the soil is sufficient. In addition, the management information in step S207 and step S208 is management information instructing an amount of water sprinkling in the subsidiary area. The information generating part 113 generates the corresponding management information by replacing $s\_1$ and $s\_th$ in FIG. 6 with $w\_1$ and $w\_th$, respectively.

In addition, the lawn mowing vehicle 20 may detect a predetermined chemical substance quantity $c\_1$ in the subsidiary area using the underground sensor 237, and store it in the storage 29 as the environment information. The predetermined chemical substance is a chemical substance contained in a nutrient in the soil in the subsidiary area. The communication part 28 transmits the environment information to the information providing device 10 via the communication network 1. The information generating part 113 generates good area information and bad area information on the basis of the state information and the environment information. The information generating part 113 generates management information corresponding to the environment information, the good area information and the bad area information.

In this case, the underground sensor 237 and the information acquisition part 111 acquire environment information and state information by replacing $s\_1$ in FIG. 6 with $c\_1$. The determining part 112 generates good area information and bad area information by replacing $s\_1$ and $s\_th$ in FIG. 6 with $c4\_1$ and $c\_th$, respectively. The $c\_th$ is a threshold of a chemical substance quantity used to determine whether an amount of predetermined nutrients in the soil is sufficient. The information generating part 113 generates the corresponding management information by replacing $s\_1$ and $s\_th$ in FIG. 6 with $c\_1$ and $c\_th$, respectively.

In this case, the management information in step S207 and step S208 is management information instructing fertilization in the subsidiary area. In addition, further, for example, the manager 7 or the like may detect an amount of chemical substances using a predetermined sensing device, without using the underground sensor 237, when the amount of chemical substances is detected.

In addition, the information acquisition part 111 may acquire an air volume k_1 in the subsidiary area as the environment information. The air volume indicates ventilation in the subsidiary area. When the ventilation is good, the growth of the lawn is promoted. The air volume k_1 may be detected by, for example, the manager 7 using an air volume sensor or the like. The information generating part 113 generates good area information and bad area information on the basis of the state information and the environment information. The information generating part 113 generates management information corresponding to the environment information, the good area information and the bad area information.

The determining part 112 may generate good area information and bad area information by replacing s_1 and s_th in FIG. 6 with k_1 and k_th, respectively. The k_th is a threshold of an air volume used to determine whether the air volume in the subsidiary area is sufficient. The information generating part 113 may generate the corresponding management information by replacing s_1 and s_th in FIG. 6 with k_1 and k_th, respectively.

In this case, the management information in step S207 and step S208 is management information instructing an increase in air volume in the subsidiary area. The manager 7 may prune trees around the subsidiary area or may replace walls around the subsidiary area with a fence on the basis of the management information displayed on the terminal device 6.

In addition, the information acquisition part 111 may acquire a particle size r_1 of soil particles in the subsidiary area as the environment information. The particle size of the soil particles correlates with drainage in the subsidiary area. When the drainage is good, the growth of the lawn is promoted. The particle size r_1 may be detected, for example, by collecting and measuring the soil of the management target area 2 by the manager 7. The information generating part 113 generates good area information and bad area information on the basis of the state information and the environment information. The information generating part 113 generates the management information corresponding to the environment information, the good area information and the bad area information.

The determining part 112 may generate good area information and bad area information by replacing s_1 and s_th in FIG. 6 with r_1 and r_th, respectively. The r_th is a threshold of an air volume used to determine whether the particle size of the soil particles in the subsidiary area is appropriate. The information generating part 113 may generate the corresponding management information by replacing s_1 and s_th in FIG. 6 with r_1 and r_th, respectively.

In this case, the management information in step S207 and step S208 is management information instructing replacement of the soil in the subsidiary area. The manager 7 may replace the soil of the subsidiary area with the soil with a large particle size on the basis of the management information displayed on the terminal device 6.

According to the above-mentioned configuration, it is possible to identify causes of growth deterioration in an area in which a growth of a lawn is not good by detecting environment information using various means, and provide management information according to the treatment with respect to the identified causes of growth deterioration.

In addition, the load sensor 235 of the lawn mowing vehicle 20 may detect a load f_1 applied to the cutting part 25 in the subsidiary area, and store it in the storage 29 as the state information.

In this case, the load sensor 235 and the information acquisition part 111 acquire state information by replacing h_1 in FIG. 6 with f_1. The information generating part 113 generates good area information and bad area information by replacing h_1 and h_th1 in FIG. 6 with f_1 and f_th1, respectively. The f_th is a threshold of a load used to determine whether a growth state of a lawn in the subsidiary area is sufficient. The information generating part 113 generates the corresponding management information by replacing h_1 and h_th1 in FIG. 6 with f_1 and f_th1, respectively.

According to the above-mentioned configuration, it is possible to identify causes of growth deterioration in an area in which a growth of lawn is not good by detecting state information using various means, and to provide management information according to the treatments with respect to the identified causes of growth deterioration.

Second Embodiment

Next, an operation of an information providing device 10 according to a second embodiment will be described focusing on differences from the first embodiment. In the second embodiment, an acidity pH of the soil in the subsidiary area is used as the environment information.

The information acquisition part 111 acquires the acidity pH of the soil in the subsidiary area as the environment information. The lawn has acidity appropriate for the growth. The acidity appropriate for the growth of the lawn varies depending upon the varieties of the lawn and has a predetermined range. While the acidity appropriate for the growth of the lawn is preferably weakly acidic, it may be weakly alkaline depending on the varieties. The acidity pH of the soil may be detected using the underground sensor 237, or may be detected using a measuring instrument after the manager 7 collects the soil. The information generating part 113 generates good area information and bad area information on the basis of the state information and the environment information. The information generating part 113 generates management information corresponding to the environment information, the good area information and the bad area information.

Figure 7:
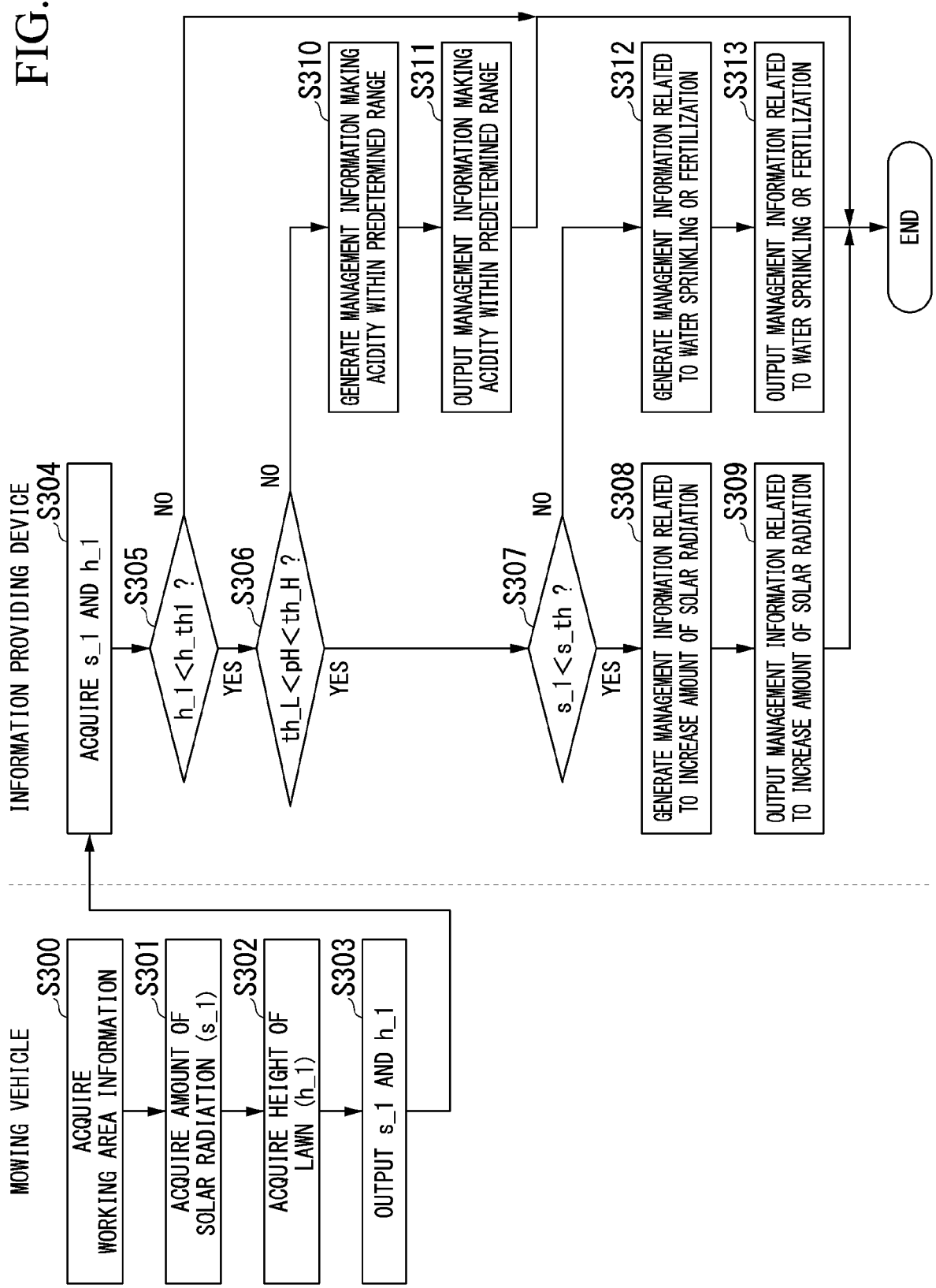
FIG. 7 is a flowchart showing operations of an information providing device and a lawn mowing vehicle according to a second embodiment of the present invention.

FIG. 7 is a flowchart showing operations of the information providing device 10 and the lawn mowing vehicle 20 according to the second embodiment of the present invention. Since the operations to step S305 are the same as the operations to step S205 of the first embodiment, description thereof will be omitted. Similarly, operations of step S307 to step S309 and step S312 to step S313 are similar to the operations of step S206 to step S210, and thus, description thereof will be omitted.

In step S306, the determining part 112 determines whether the detected pH is between th_L and th_H. When the detected pH is between th_L and th_H, the determining part 112 advances the processing to step S307. When the detected pH is not between th_L and th_H, the determining part 112 advances the processing to step S310.

In step S310, the information generating part 113 generates management information instructing to make the acidity of the soil of the subsidiary area between th_L and th_H, and advances the processing to step S311. In step S311, the information generating part 113 outputs the management information instructing to make the acidity of the soil in the subsidiary area between th_L and th_H, and terminates the processing.

The communication part 13 transmits the management information generated and output by the information generating part 113 to the terminal device 6 via the communication network 1. The manager 7 may make the soil of the subsidiary area between th_L and th_H by replacing the soil of the subsidiary area or spray a predetermined medicine on the basis of the management information displayed on the terminal device 6.

According to the above-mentioned configuration, it is possible to identify the causes of growth deterioration in the area in which the growth of the lawn is not good according to the acidity of the soil and to provide the management information according to the treatments with respect to the identified causes of growth deterioration by using the acidity of the soil in the subsidiary area as the environment information.

Third Embodiment

Next, an operation of an information providing device 10 according to a third embodiment will be described focusing on differences from the first and second embodiments.

Figure 8:
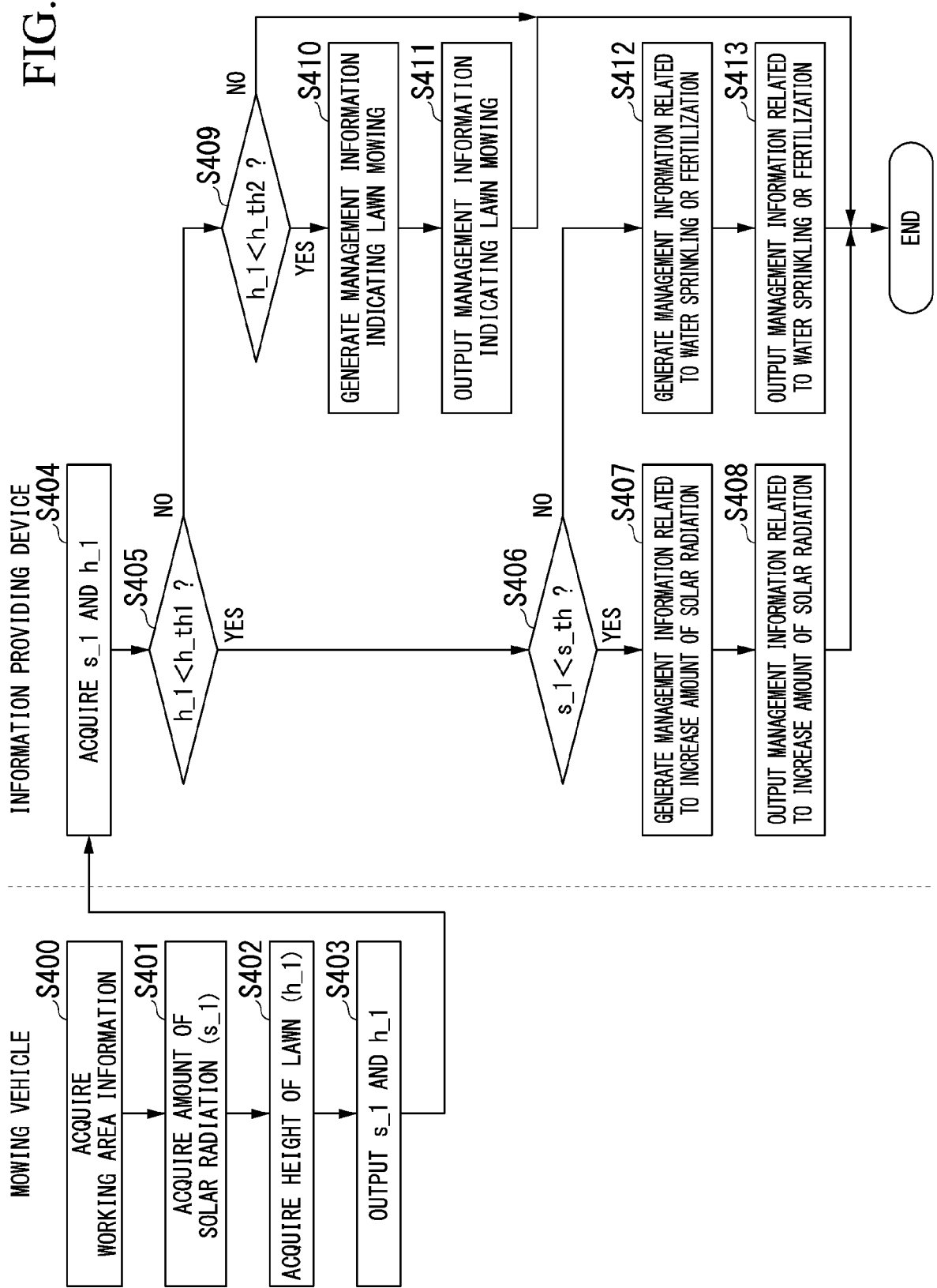
FIG. 8 is a flowchart showing operations of an information providing device and a lawn mowing vehicle according to a third embodiment of the present invention.

FIG. 8 is a flowchart showing operations of the information providing device 10 and the lawn mowing vehicle 20 according to the third embodiment of the present invention. First, since the operations to step S408 and the operations of step S412 to step S413 are similar to those of the first embodiment, description thereof will be omitted.

In step S409, the determining part 112 determines whether h_1 is greater than h_th2. The h_th2 is a second threshold of a height of a lawn, which is greater than h_th1. The h_th2 is a threshold indicating that the lawn is excessively grown. In other words, the h_th2 is a threshold used to determine whether the subsidiary area is the fourth area.

In step S409, when h_1 is greater than h_th2, the determining part 112 advances the processing to step S410. In step S409, when h_1 is equal to or smaller than h_th2, the determining part 112 terminates the processing.

In step S410, the information generating part 113 generates management information instructing to perform lawn mowing such that the height of the lawn in the subsidiary area is equal to or smaller than h_th2, and advances the processing to step S411. In step S411, the information generating part 113 outputs the generated management information, and terminates the processing.

The communication part 13 transmits the management information generated and output by the information generating part 113 to the terminal device 6 via the communication network 1. The manager 7 performs treatment corresponding to the management information on the basis of the management information displayed on the terminal device 6.

As described above, the information generating part 113 of the information providing device 10 according to the embodiment generates good area information and bad area information in the subsidiary area on the basis of the acquired environment information and state information. The information generating part 113 generates management information indicating treatments corresponding to the environment information, the good area information and the bad area information. The information generating part 113 generates and outputs the management information instructing to make the lawn excessively grown to a too great height lower than the predetermined height.

According to the configuration, it is possible to arrange the landscape by not only identifying the causes of growth deterioration in the area in which the growth of the lawn is not good and providing management information related to the treatment with respect to the identified causes of growth deterioration but also mowing the excessively grown lawn.

In addition, the area in which the lawn excessively grown may include excessively grown weeds. Accordingly, it is possible not only to improve the aesthetics of the lawn-mown area but also to distribute water or nutrients to the lawn by mowing the excessively grown weeds in addition to the lawn.

Fourth Embodiment

Next, an operation of an information providing device 10 according to a fourth embodiment will be described focusing on differences from the first to third embodiments.

Figure 9:
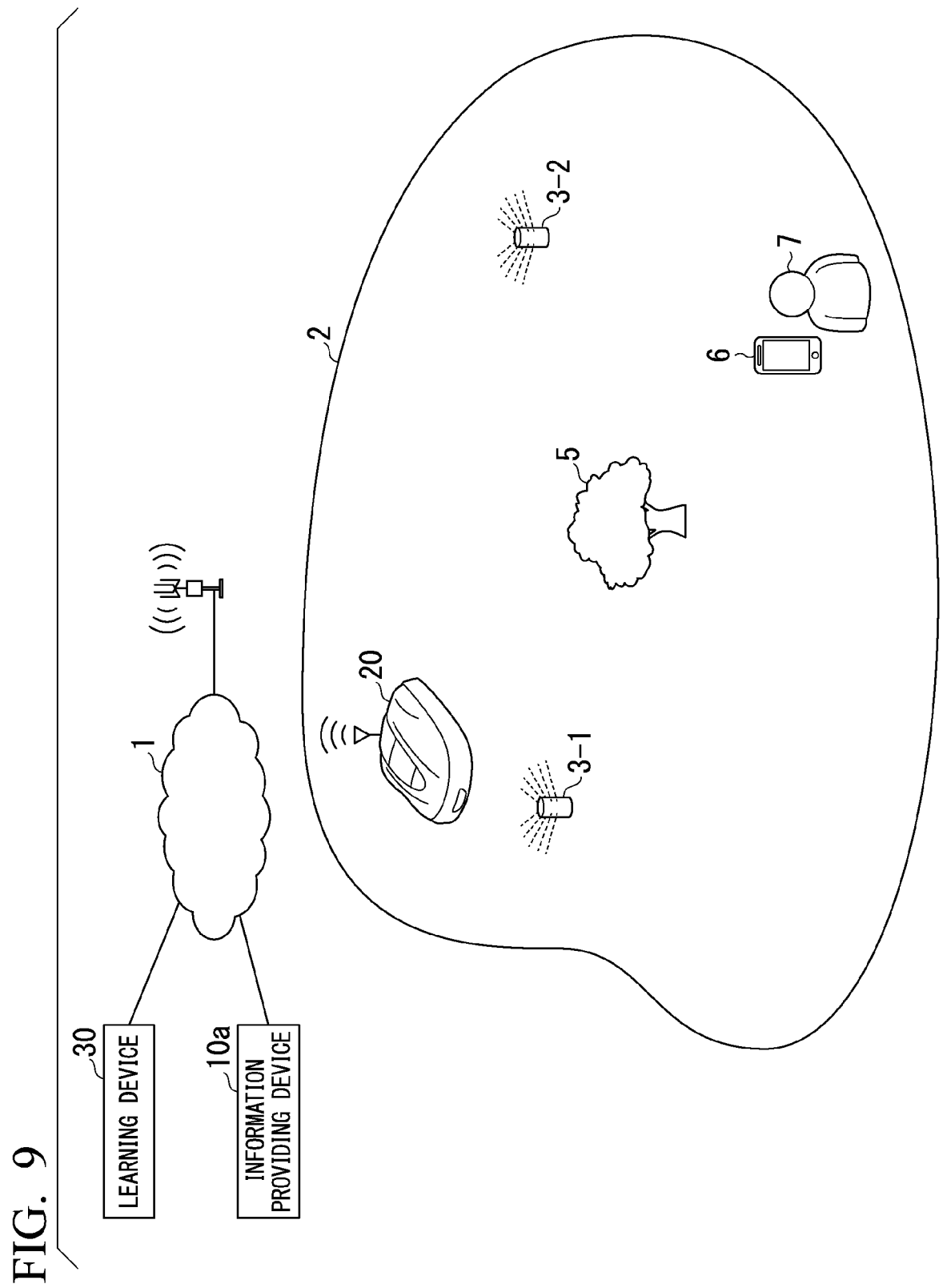
FIG. 9 is a configuration view of a lawn mowing management system according to a fourth embodiment of the present invention.

FIG. 9 is a configuration view of a lawn mowing management system according to the fourth embodiment of the present invention. The lawn mowing management system according to the fourth embodiment of the present invention includes a learning device 30. This point is different from the first to third embodiments. The learning device 30 is connected to the communication network 1. In addition, as described below, the information providing device 10a includes an execution processing part 114. The lawn mowing management system according to the embodiment mainly performs two-step processing. The two-step processing includes (I) a learning step by the learning device 30, and (II) a management information estimating step by the execution processing part 114.

Figure 10:
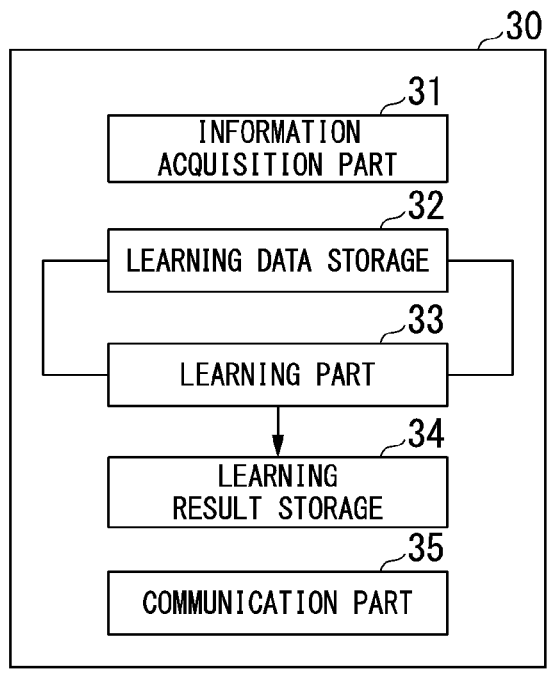
FIG. 10 is a functional block diagram of a learning device according to the fourth embodiment of the present invention.

FIG. 10 is a configuration view of the learning device 30 according to the fourth embodiment of the present invention. The learning device 30 includes an information acquisition part 31, a learning data storage 32, a learning part 33, a learning result storage 34 and a communication part 35. The information acquisition part 31 acquires a photographed image as an instructor data and management information corresponding to the photographed image, and stores them in the learning data storage 32. The learning part 33 performs machine learning by using the instructor data in which the photographed image is set as input and the management information is set as output, and generates a learnt model as a learning result. The learning part 33 stores the learnt model in the learning result storage 34. The photographed image is a photographed image of each lawn mowing area in the management target area 2. The communication part 35 acquires the learnt model from the learning result storage 34, and transmits it to the outside.

The learning part 33 recursively calculates parameters that constitute a model such that a difference between the output corresponding to the input and the target output becomes small by using the instructor data of a plurality of sets. The learning part 33 performs, for example, deep learning when the model is required. The deep learning is machine learning using a multiple layer structure, in particular, a neural network with three or more layers. As the neural network of the multiple layer structure, for example, a convolutional network can be used. The neural network may be another neural network such as a perceptron neural network, a recurrent neural network, a residual network, or the like.

Next, an operation when the learning device 30 generates a learnt model will be described. First, the information acquisition part 31 acquires a photographed image of a lawn mowing area, and stores it in the learning data storage 32.

The information acquisition part 31 acquires management information corresponding to the photographed image, and stores it in the learning data storage 32. Next, the learning part 33 performs machine learning using the photographed image and the management information as the instructor data, and generates the learnt model as the learning result. The learning part 33 outputs the learnt model and stores it in the learning result storage 34.

Figure 11:
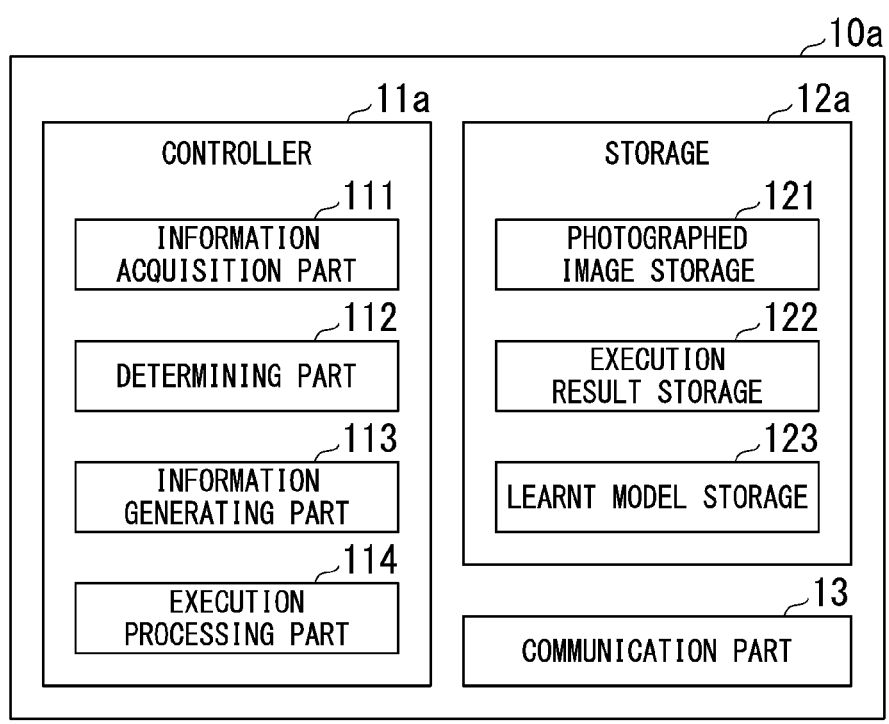
FIG. 11 is a functional block diagram of an information providing device according to the fourth embodiment of the present invention.

FIG. 11 is a configuration view of an information providing device 10a according to the fourth embodiment of the present invention. Unlike the first to third embodiments, a controller 11a includes an execution processing part 114. In addition, a storage 12a includes a photographed image storage 121, an executed result storage 122 and a learnt model storage 123. The information acquisition part 111 acquires a photographed image, and stores it in the photographed image storage 121. In addition, the information acquisition part 111 acquires a learnt model, and stores it in the learnt model storage 123.

The execution processing part 114 reads the photographed image from the photographed image storage 121, estimates the management information using the neural network based on a learnt model 124, and stores it in the executed result storage 122. The communication part 13 reads the estimated management information from the executed result storage 122, and transmits it to the outside. The manager 7 receives the management information via the terminal device 6. The manager 7 executes treatment corresponding to the management information.

Next, an example of the instructor data will be described. The instructor data according to the embodiment is a photographed image of a lawn mowing area in the management target area 2, and management information indicating treatment in the lawn mowing area. For example, the management information may be an instruction related to an increase in amount of solar radiation in the lawn mowing area, an instruction related to a predetermined amount of water sprinkling or a predetermined amount of fertilization, or an instruction related to a traveling limit of the lawn mowing vehicle 20, or an instruction of mowing overgrown lawn or weeds.

Figures 12, 13:
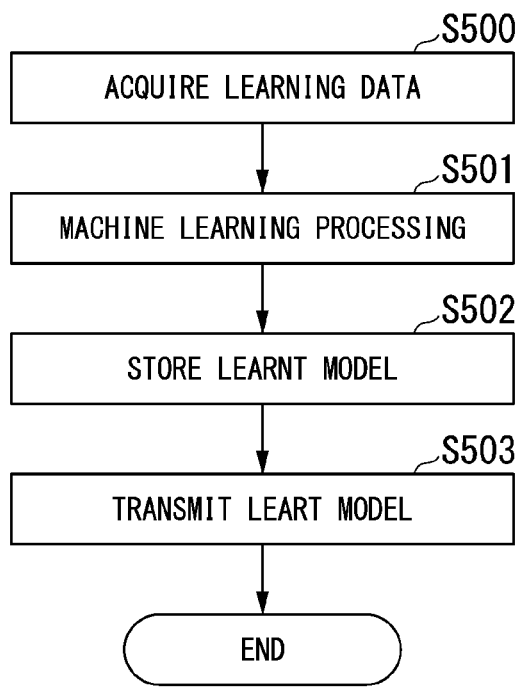
FIG. 12 is a table showing correspondence between a photographed image of a lawn mowing area and management information according to the fourth embodiment of the present invention.
FIG. 13 is a flowchart showing an operation of a learning device according to the fourth embodiment of the present invention.

FIG. 12 is an example of the instructor data according to the embodiment. A column A in FIG. 12 indicates photographed image file information in the lawn mowing area. A column B in FIG. 12 is a table indicating correspondence between image files written in the column A and management information corresponding to these. In FIG. 12, management information with "a traveling limit" is associated with images from 0001.jpg to 1000.jpg. In the images from 0001.jpg to 1000.jpg, brown or black soil is exposed in the photographing area and the images from 0001.jpg to 1000.jpg have a high correlation with the fact that a growth state of a lawn is not good. In other words, the images from 0001.jpg to 1000.jpg have a high correlation with the fact that the area of the photographed image is a first area. Accordingly, the management information with "the traveling limit" indicates that entry of a person or traveling of the lawn mowing vehicle 20 into the area in which such an image is photographed is limited.

The management information with "chemical spray for a large patch" is associated with images from 1001.jpg to 2000.jpg. The images from 1001.jpg to 2000.jpg include disease-specific colors or patterns called large patches (brown patch). Such photographed images have a high correlation with the fact that the lawn is suffering from large patches. In other words, the images from 1001.jpg to 2000.jpg have a high correlation with the fact that the area of the photographed image is a second area. Accordingly, the management information with "the chemical spray for a large patch" promotes spraying of medicine for a large patch.

The management information with "chemical spray for a rust disease" is associated with images from 2001.jpg to 3000.jpg. The images from 2001.jpg to 3000.jpg include disease-specific colors or patterns called rust disease. In other words, the images from 2001.jpg to 3000.jpg have a high correlation with the fact that the area of the photographed image is a second area. Such photographed images have a high correlation with the fact that the lawn is suffering from rust disease. Accordingly, the management information with "the chemical spray for a rust disease" promotes spraying of medicine for a rust disease.

Management information with "treatment not necessary" is associated with images from 3001.jpg to 4000.jpg. The images from 3001.jpg to 4000.jpg have a high correlation with the fact that the particular abnormalities seen in 0001.jpg to 3000.jpg are not contained in the lawn mowing area. In other words, the images from 3001.jpg to 4000.jpg have a high correlation with the fact that the area of the photographed image is a third area. Accordingly, the management information with "treatment not necessary" notifies that no special treatments are required.

The information acquisition part 31 acquires the photographed image written in FIG. 12 and the management information corresponding to the photographed image, and stores them in the learning data storage 32. The learning part 33 performs machine learning by using instructor data in which the photographed image is set as input and the management information is set as output, and generates a learnt model as a learning result. The learning part 33 stores the generated learnt model in the learning result storage 34. The communication part 35 reads the learnt model from the learning result storage 34, and transmits it to the information providing device 10a via the communication network 1.

The information acquisition part 111 acquires the learnt model via the communication part 13, and stores it in the learnt model storage 123. The information acquisition part 111 acquires, for example, the photographed image in the subsidiary area, and stores it in the photographed image storage 121. The execution processing part 114 estimates the management information corresponding to the photographed image by using the neural network based on the learnt model stored in the learnt model storage 123, and stores it in the executed result storage 122. The communication part 13 transmits the obtained management information. The manager 7 acquires management information via the terminal device 6, and executes treatment corresponding to the management information. The treatment corresponding to the management information is, for example, treatment written in the column B in FIG. 12.

FIG. 13 is a flowchart showing an operation of the learning device 30 according to the fourth embodiment of the present invention. In step S500, the information acquisition part 31 acquires the photographed image and the management information written in FIG. 12 as the instructor data. In step S501, the learning part 33 performs machine learning based on the instructor data stored in the learning data storage 32. In step S502, the learning part 33 stores the learning result in the learning result storage 34 as the learnt model. In step S503, the communication part 35 transmits the learnt model.

Figure 14:
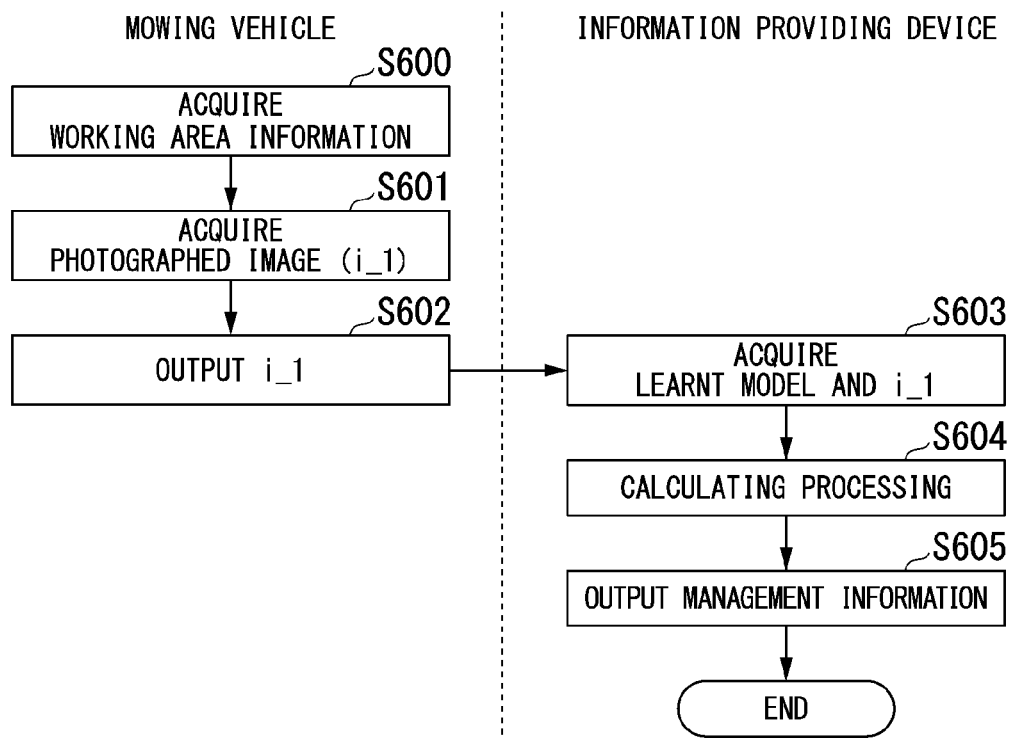
FIG. 14 is a flowchart showing operations of the information providing device and the lawn mowing vehicle according to the fourth embodiment of the present invention.

FIG. 14 is a flowchart showing operations of the information providing device 10 and the lawn mowing vehicle 20 according to the fourth embodiment of the present invention.

In step S600, the controller 22 acquires information of the subsidiary area, and stores it in the storage 29. In step S601, the camera 231 photographs the subsidiary area, and stores it in the storage 29 as environment information i_1 of the subsidiary area. In step S602, the communication part 28 reads the i_1 from the storage 29, and outputs it to the information providing device 10 via the communication network 1.

Next, an operation of causing the information providing device 10 to acquire environment information and state information, and to generate and output management information on the basis of the environment information and the state information will be described. In step S603, the information acquisition part 111 acquires the i_1 and learnt model via the communication network 1 using the communication part 13. The information acquisition part 111 stores the i_1 in the photographed image storage 121, and stores the learnt model in the learnt model storage 123. In step S604, the execution processing part 114 performs calculation processing using a photographed image i_1 as an input on the basis of the learnt model stored in the learnt model storage 123. In step S605, the information generating part 113 outputs the management information output as a result of the calculation processing in step S604.

The communication part 13 transmits the management information generated and output by the information generating part 113 to the terminal device 6 via the communication network 1. The manager 7 performs treatment corresponding to the management information on the basis of the management information displayed on the terminal device 6.

As described above, the lawn mowing management system according to the embodiment includes the information providing device 10a and the learning device 30. The information providing device 10a includes the controller 11a, the storage 12 and the communication part 13. The controller 11a includes the information acquisition part 111, the information generating part 113, the determining part 112 and the execution processing part 114. The learning device 30 generates a learnt model by performing machine learning on the basis of the photographed image and the management information of the lawn mowing area. The information acquisition part 111 acquires, for example, the photographed image of the subsidiary area in the management target area 2. The execution processing part 114 estimates and outputs the management information indicating the treatment corresponding to the photographed image.

According to the configuration, it is possible to provide the management information related to the treatment for improving the growth environment of the lawn in the subsidiary area on the basis of the photographed image of the subsidiary area in the management target area 2.

In addition, the execution processing part 114 may predict management information corresponding to a photographed image by inputting a photographed image of a lawn mowing area in a management target area 2' adjacent to the management target area 2 using the learnt model based on the photographed image and the management information of the lawn mowing area in the management target area 2.

Accordingly, without newly acquiring the environment information or the state information in the management target area 2' adjacent thereto, it is possible to provide the management information according to the treatment for improving the growth environment of the lawn on the basis of the learnt model which is acquired in the management target area 2 and the photographed image of the lawn mowing area in the management target area 2' adjacent thereto.

Fifth Embodiment

Next, an operation of a lawn mowing vehicle 20b according to a fifth embodiment will be described focusing on differences from the first to fourth embodiments. The lawn mowing vehicle 20b according to the embodiment is the same as that of the first to third embodiments except a configuration and a function of a controller 22b. The controller 22b of the lawn mowing vehicle 20b includes the same configuration and function as those of the controller 11 of the information providing device 10 according to the first to third embodiments.

In other words, the lawn mowing vehicle 20b includes the information providing device 10 according to the first to third embodiments. The lawn mowing vehicle 20b generates and outputs the management information on the basis of the environment information in the lawn mowing area and the state information related to the growth state of the lawn, in addition to the functions of the lawn mowing vehicle 20 according to the first to third embodiments.

Figure 15:
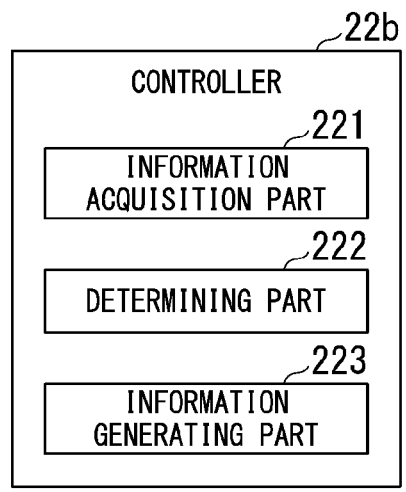
FIG. 15 is a functional block configuration view of a controller included in a lawn mowing vehicle according to a fifth embodiment of the present invention.

FIG. 15 is a functional block configuration view of the controller 22b included in the lawn mowing vehicle 20b according to the fifth embodiment. The controller 22b includes an information acquisition part 221, an information generating part 222 and a determining part 223. Since the operations of the information acquisition part 221, the information generating part 222 and the determining part 223 are the same as those of the information acquisition part 111, the information generating part 113 and the determining part 112 according to the first to fourth embodiments, description thereof will be omitted.

As described above, the lawn mowing vehicle 20b according to the embodiment includes the display 21, the controller 22b, the sensor 23, the cutting part 25, the motor 26, the wheels 27, the communication part 28 and the storage 29. The controller 22a includes the information acquisition part 221, the information generating part 222 and the determining part 223. The information acquisition part 221 acquires the environment information and the state information in the lawn mowing area from the sensor 23. The information generating part 222 generates and outputs the management information based on the environment information and the state information.

According to the configuration, the lawn mowing vehicle 20b can identify the causes of growth deterioration in the area in which the growth of the lawn is not good without using the information providing device 10, and provide the management information according to the treatment with respect to the identified causes of growth deterioration.

Conclusion of Embodiments

The embodiments disclose at least an information providing device, a lawn mowing vehicle and a lawn mowing management system, which will be described below.

1. An information providing device (for example, 10) of the embodiment includes:

an information acquisition part configured to acquire environment information which indicates a growth environment of grass in a predetermined area and state information which indicates a growth state of the grass in the predetermined area; and an information generating part configured to generate good area information which indicates an area in which the growth state of the grass in the predetermined area is good and bad area information which indicates an area in which the growth state of the grass in the predetermined area is bad based on the state information, and configured to generate management information which indicates treatment corresponding to the environment information, the good area information and the bad area information.

According to the embodiment, it is possible to identify causes of growth deterioration in the area in which a growth of grass is not good and to provide management information related to treatment corresponding to the identified causes of growth deterioration.

2. According to the embodiment,
the environment information indicates at least one of an amount of moisture contained in the soil, an amount of predetermined chemical substances contained in the soil, an amount of solar radiation, and an air volume in the predetermined area.

According to the embodiment, it is possible to identify causes of growth deterioration in an area in which growth of grass is not good and to provide management information related to treatment corresponding to the identified causes of growth deterioration by detecting environment information using various means.

3. According to the embodiment,
the information acquisition part acquires the state information based on a height of the grass from the ground.

According to the embodiment, a growth state of grass can be directly and accurately detected. Accordingly, the treatment corresponding to the management information can be executed in an appropriate mowing area.

4. According to the embodiment, the management information indicates a type of medicine sprayed with respect to the area in which the growth state of the grass is bad.

According to the embodiment, it is possible to accurately improve a growth environment of an area in which a growth state of grass is bad by promoting spraying of medicine appropriate for the area in which the growth state of the grass is bad.

5. According to the embodiment, the management information indicates an amount of water sprayed with respect to the area in which the growth state of the grass is bad.

According to the embodiment, it is possible to accurately improve a growth environment of an area in which a growth state of grass is bad by notifying an appropriate amount of water sprayed to the area in which the growth state of the grass is bad.

6. The management information indicates to mow the grass in the area in which the growth state of the grass is good more than the grass in the area in which the growth state of the grass is bad.

According to the embodiment, it is possible to improve a growth environment and landscape in a mowing area by urging to mow grass whose growth state is too good or overgrown weeds.

7. According to the embodiment,
the state information includes photographed image information of grass in the predetermined area,
the information generating part generates the good area information when the photographed image information of the grass does not include a predetermined color or pattern, and generates the bad area information when the photographed image information of the grass includes the predetermined color or pattern, and
the predetermined color or pattern indicates either that the grass has a predetermined disease or that the soil is exposed in the predetermined area.

According to the embodiment, it is possible to urge treatment appropriate to improve a growth state or a growth environment of grass by accurately detecting the growth state or the growth environment of the grass on the basis of the photographed image in the mowing area.

8. According to the embodiment, the state information is provided based on a load applied to a rotary knife when a mowing vehicle operated in the predetermined area mows the grass.

According to the embodiment, detection accuracy of a growth state of grass can be increased. Accordingly, treatment corresponding to management information can be executed in an appropriate mowing area.

9. According to the embodiment, the management information indicates that traveling of the mowing vehicle in the area in which the growth state of the grass is bad is limited.

According to the embodiment, in the area in which the growth environment of the grass is deteriorated, further deterioration of the growth environment can be suppressed.

10. A mowing vehicle (for example, 20) of the embodiment includes:
a mowing part having a rotary knife driven by a prime mover;
a sensor configured to acquire environment information indicating a growth environment of a grass in a predetermined area;
a state information acquisition part configured to acquire state information indicating the growth state of the grass in an area in which the mowing is performed; and
a communication part configured to transmit the environment information and the state information and receive management information indicating treatment corresponding to the environment information, good area information and bad area information,
wherein the good area information indicates an area in which the growth state of the grass in the predetermined area is good and is generated based on the state information, and
the bad area information indicates an area in which the growth state of the grass in the predetermined area is bad and is generated based on the state information.

According to the embodiment, it is possible to identify causes of growth deterioration in an area in which growth of grass is not good and to provide management information related to treatment corresponding to the identified causes of growth deterioration by using a single mowing vehicle.

11. A mowing management system of the embodiment includes:
a mowing vehicle including
a mowing part having a rotary knife driven by a prime mover,
a sensor configured to acquire environment information indicating a growth environment of a grass in a predetermined area,
a state information acquisition part configured to acquire state information indicating the growth state of grass in the predetermined area, and
a communication part configured to transmit the environment information and the state information and configured to receive management information which indicates treatment corresponding to the environment information, good area information and bad area information, the good area information indicating an area in which the growth state of the grass is good in an area in which the mowing is performed, the bad area information indicating an area in which the growth state of grass is bad in an area in which the mowing is performed; and an information providing device including
- a state acquisition part configured to acquire the environment information and the state information, and
- an information generating part configured to generate the good area information and the bad area information based on the state information and configured to generate and output the management information corresponding to the environment information, the good area information and the bad area information.

According to the embodiment, it is possible to identify causes of growth deterioration in an area in which growth of grass is not good, and provide management information related to treatment with respect to the identified causes of growth deterioration.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An information providing device comprising:
an information acquisition part configured to acquire environment information which indicates a growth environment of grass in a predetermined area and state information which indicates a growth state of the grass in the predetermined area; and
an information generating part configured to determine a good area which indicates an area in which the growth state of the grass in the predetermined area is good and a bad area which indicates an area in which the growth state of the grass in the predetermined area is bad based on the state information, and configured to generate management information which indicates a content of treatments to be performed with respect to the good area and the bad area based on the environment information,
wherein the state information is provided based on a load applied to a rotary knife when a mowing vehicle operated in the predetermined area mows the grass.

2. The information providing device according to claim 1, wherein the environment information indicates at least one of an amount of moisture contained in a soil, an amount of predetermined chemical substances contained in the soil, an amount of solar radiation, and an air volume in the predetermined area.

3. The information providing device according to claim 1, wherein the information acquisition part acquires the state information based on a height of the grass from a ground.

4. The information providing device according to claim 1, wherein the management information indicates a type of medicine sprayed with respect to the area in which the growth state of the grass is bad.

5. The information providing device according to claim 1, wherein the management information indicates an amount of water sprayed with respect to the area in which the growth state of the grass is bad.

6. The information providing device according to claim 1, wherein the management information indicates to mow the grass in the area in which the growth state of the grass is good more than the grass in the area in which the growth state of the grass is bad.

7. The information providing device according to claim 1, wherein the state information includes photographed image information of grass in the predetermined area,
the information generating part generates the good area information when the photographed image information of the grass does not include a predetermined color or pattern, and generates the bad area information when the photographed image information of the grass includes the predetermined color or pattern, and
the predetermined color or pattern indicates either that the grass has a predetermined disease or that the soil is exposed in the predetermined area.

8. The information providing device according to claim 1, wherein the management information indicates that traveling of the mowing vehicle in the area in which the growth state of the grass is bad is limited.

9. A mowing vehicle comprising:
a mowing part having a rotary knife driven by a prime mover;
a sensor configured to acquire environment information indicating a growth environment of a grass in a predetermined area;
a state information acquisition part configured to acquire state information indicating the growth state of the grass in an area in which the mowing is performed; and
a communication part configured to transmit the environment information and the state information and receive management information indicating treatment corresponding to the environment information, good area information and bad area information,
wherein the good area information indicates an area in which the growth state of the grass in the predetermined area is good and is generated based on the state information, and
the bad area information indicates an area in which the growth state of the grass in the predetermined area is bad and is generated based on the state information,
wherein the state information is provided based on a load applied to a rotary knife when the mowing vehicle operated in the predetermined area mows the grass.

10. A mowing management system comprising:
a mowing vehicle including
- a mowing part having a rotary knife driven by a prime mover,
- a sensor configured to acquire environment information indicating a growth environment of a grass in a predetermined area,
- a state information acquisition part configured to acquire state information indicating the growth state of the grass in the predetermined area, and
- a communication part configured to transmit the environment information and the state information and configured to receive management information which indicates treatment corresponding to the environment information, good area information and bad area information, the good area information indicating an area in which the growth state of the grass is good in an area in which the mowing is performed, the bad area information indicating an area in which the growth state of grass is bad in an area in which the mowing is performed; and an information providing device including
- a state acquisition part configured to acquire the environment information and the state information, and
- an information generating part configured to generate the good area information and the bad area information based on the state information and configured to generate and output the management information corresponding to the environment information, the good area information and the bad area information, wherein the state information is provided based on a load applied to a rotary knife when the mowing vehicle operated in the predetermined area mows the grass.

* * * * *